(12) United States Patent
Rink et al.

(10) Patent No.: US 7,601,765 B2
(45) Date of Patent: Oct. 13, 2009

(54) UV-ACTIVE BINDING AGENT

(75) Inventors: Heinz-Peter Rink, Münster (DE);
Susanne Neumann, Münster (DE); Uwe Meisenburg, Mannheim (DE);
Karl-Heinz Joost, Drensteinfurt (DE);
Dietmar Häring, Schriesheim (DE);
Bernhard Hauer, Fußgönheim (DE)

(73) Assignee: BASF Coatings AG, Munster (DE)

( * ) Notice: Subject to any disclaimer, the term of this patent is extended or adjusted under 35 U.S.C. 154(b) by 509 days.

(21) Appl. No.: 10/532,575

(22) PCT Filed: Nov. 5, 2003

(86) PCT No.: PCT/EP03/12322

§ 371 (c)(1),
(2), (4) Date: Nov. 11, 2005

(87) PCT Pub. No.: WO2004/042069

PCT Pub. Date: May 21, 2004

(65) Prior Publication Data

US 2006/0148975 A1    Jul. 6, 2006

(30) Foreign Application Priority Data

Nov. 5, 2002    (DE) ................... 102 51 729

(51) Int. Cl.
*C08F 2/46* (2006.01)
*C08F 2/00* (2006.01)
*C08F 2/38* (2006.01)
*C08F 22/10* (2006.01)
*C08F 22/00* (2006.01)

(52) U.S. Cl. .............. 522/153; 522/150; 522/178; 522/182; 522/912; 522/104; 526/317.1; 526/318; 526/318.4; 526/319; 526/320; 526/328; 526/328.5; 526/329.5; 526/329.7; 528/271; 528/272; 528/274; 524/700; 524/704; 524/800; 524/804; 524/849; 524/851; 524/878

(58) Field of Classification Search ............. 526/317.1, 526/318, 318.4, 319, 320, 328, 328.5, 329.5, 526/329.7; 528/271, 272, 274; 524/700, 524/704, 800, 804, 849, 851, 878, 932; 522/104, 522/107, 178, 182, 912, 150, 153
See application file for complete search history.

(56) References Cited

U.S. PATENT DOCUMENTS

| 6,268,521 B1 | 7/2001 | Gruning et al. ............. 560/209 |
| 6,288,129 B1 | 9/2001 | Gruning et al. ............. 516/23 |
| 2003/0036604 A1 | 2/2003 | Meisenburg et al. ........ 525/123 |

FOREIGN PATENT DOCUMENTS

| DE | 10305076 A1 | * 8/2004 |
| EP | 0 999 229 | 10/1999 |
| EP | 0 999 230 | 10/1999 |
| WO | WO01/46286 | 6/2001 |

OTHER PUBLICATIONS

E. Marechal et al., Polymer Bulletin 26, pp. 55 to 62 (1991).
H. RiHer et al., Polymer Bulletin 21, pp. 535 to 540 (1989).
H. RiHer et al., Makromel. Chem193, Enzymes in polymer chemistry, 6, pp. 323 to 328 (1992).
A. Tor et al., Enzyme and Microbial Technology, stoneham, MA, US, Apr. 12, 1990, pp. 229-304, XP-000910508.
International Search Report of PCT/EP2003/012322 dated Mar. 23, 2004.

* cited by examiner

*Primary Examiner*—Sanza L McClendon
(74) *Attorney, Agent, or Firm*—Cantor Colburn LLP

(57) ABSTRACT

The present invention relates to processes for preparing actinic-radiation-curable and/or dual-cure poly(meth)acrylates by preparing a poly(meth)acrylate containing hydroxy-functional side chains and transesterifying or esterifying the poly(meth)acrylate containing hydroxy-functional side chains with a (meth)acrylate or (meth)acrylic acid. The present invention further relates to the actinic-radiation-curable and/or dual-cure poly(meth)acrylates themselves and to the use of the actinic-radiation-curable and/or dual-cure poly(meth)acrylates in the preparation of dispersions or as a component in coating formulations and topcoats comprising at least one actinic-radiation-curable and/or dual-cure poly(meth)acrylate.

16 Claims, No Drawings

UV-ACTIVE BINDING AGENT

CROSS REFERENCE TO RELATED APPLICATIONS

This application is a National Phase Application of Patent Application PCT/EP2003/012322 filed 5 Nov. 2003, which claims priority to DE 10251729.0, filed on 5 Nov. 2002.

The invention relates to a process for preparing radiation-curable and/or dual-cure poly(meth)acrylates, to the poly(meth)acrylates themselves, to their use as a component in the preparation of dispersions or as a component in coating formulations, to coating formulations comprising the poly(meth)acrylates of the invention and to a process for preparing the coating formulations and their use.

UV-curable and dual-cure poly(meth)acrylates are of particular interest for use in topcoats. Poly(meth)acrylates generally have excellent outdoor weather stabilities. In conjunction with a UV curing technology, additional advantages are achievable. For example, the scratch resistance of the coating can be increased significantly, with an attendant improvement in coating performance. Particularly important, however, are improvements in application, in particular a very rapid drying of the coating materials. This property is critical for rapid processing technologies.

In accordance with the prior art, UV-curable polyacrylates are reacted by copolymerizing glycidyl methacrylate followed by thermal reaction with acrylic acid in the presence of a catalyst (DE-A 2 436 186, EP-A 0 650 978). Disadvantages associated with this prior art mode of preparation are the attendant secondary reactions and deteriorations in color. In view of the reaction conditions; particularly the high temperatures, under which the reaction is carried out it is absolutely necessary to use stabilizers in order to prevent the free-radical polymerization of the acrylic acid used.

A conventional acidic esterification of poly(meth)acrylates containing hydroxy-functional side chains with acrylic acid is not possible, since in the course of such reaction the ester bonds of the poly(meth)acrylate are cleaved.

Known from the prior art is the functionalization of polymeric compounds with (meth)acrylic acid and/or (meth)acrylic esters.

EP-A 0 999 230 and EP-A 0 999 229 relate to processes for preparing (meth)acrylic esters of hydroxy-functional siloxanes and/or polyalkylene-modified siloxanes ('230) and also of polyoxyalkylenes ('229) by esterification or transesterification of the siloxanes or polyoxyalkylenes, respectively, with (meth)acrylic acid and/or (meth)acrylic esters in the presence of an enzyme. According to EP-A 0 999 230 and EP-A 0 999 229, however, only the specific polymers referred to are reacted with (meth)acrylic acid and/or (meth)acrylic esters. There is no mention of a reaction of poly(meth)acrylates.

E. Marechal et al., Polymer Bulletin 26, 55 to 62 (1991) relates to the transesterification of oligo(methacrylates) containing terminal ester groups with allyl alcohol in the presence of lipase. Transesterification takes place only at the terminal groups.

H. Ritter et al., Polymer Bulletin 21, 535 to 540 (1989) relates to the lipase catalyzed acetylation of methacrylic acid polymers containing OH groups. The acetylation takes place in the presence of vinyl acetate. Reaction with vinyl acetate produces a very good leaving group, with the aldehyde formed being easily removable from the reaction mixture. Nevertheless, the reaction time amounts to 2 to 1 days.

H. Ritter et al., Makromol. Chem. 193, 323 to 328 (1992) relates to the enzymatically catalyzed acylation of OH-containing comblike methacrylic acid polymers with active esters, such as vinyl acetate, phenyl acetate, 4-fluorophenyl acetate, and phenyl stearate. There is no mention of an esterification of the polymers with acrylates. The reaction times of the reaction according to Ritter et al. are very long (2, 4 and 6 days).

The object of the present invention is to provide a gentle and selective process for preparing poly(meth)acrylates functionalized with (meth)acrylic acid and/or (meth)acrylates which is more variable than the known preparation process starting from glycidyl methacrylate, is able to start from less expensive starting substances, and allows a gentler preparation, so that new kinds of poly(meth)acrylates substituted by (meth)acrylic groups are obtainable.

The object is achieved by a process for preparing UV-curable and/or dual-cure poly(meth)acrylates, comprising the following steps:

a) preparing a poly(meth)acrylate containing hydroxy-functional side chains by polymerizing
   aa) at least one (meth)acrylate of the general formula (I) as component A

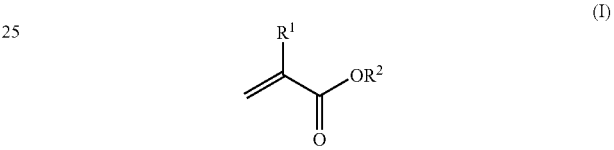

in which
$R^1$ is H, $CH_3$ or $CH_2OH$ and
$R^2$ is an alkyl or cycloalkyl radical which is unsubstituted or substituted by functional groups such as acrylic, ether, amino, epoxy, halogen or sulfonic acid groups, preferably a $C_1$ to $C_{18}$ alkyl radical, more preferably a $C_1$ to $C_8$ alkyl radical, very preferably a $C_1$ to $C_8$ alkyl radical unsubstituted by functional groups, in particular a methyl, ethyl, n-propyl, isopropyl, n-butyl, isobutyl, 2-ethylhexyl, tert-butyl, cyclohexyl, tert-butylcyclohexyl, isobornyl or trimethylcyclohexyl radical; and ab) at least one hydroxyalkyl (meth)acrylate of the general formula (II) as component B

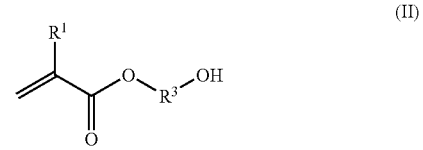

in which
$R^1$ is H, $CH_3$ or $CH_2OH$ and
$R^3$ is $-(CH_2)_n-$, $-CH_2-CH(CH_3)-CH_2-$ or $-CH_2CH(CH_3)-$ or $-CH(CH_3)CH_2-$ or

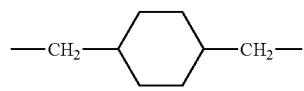

n is at least 2, preferably 2 to 8, more preferably 2 to 6, very preferably 2 to 4, the hydroxyalkyl (meth)acrylate of the general formula (II) being selected in particular from the group consisting of 2-hydroxyethyl(meth)acrylate, 2-hydroxypropyl (meth)acrylate or hydroxybutyl (meth)acrylate; and ac) if desired, further comonomers, copolymerizable with the (meth)acrylates of the general formula (I) and (II), as component C, preferably selected from the group consisting of styrene, acrylonitrile, vinyl acetate, vinyl propionate, vinyl chloride, vinylidene chloride, butadiene, and adducts of Versatic acid glycide residues and unsaturated acids, especially (meth)acrylic acid, and ad) if desired, auxiliary monomers as component D preferably selected from the group consisting of (meth) acrylic acid, itaconic acid, maleic acid, fumaric acid, crotonic acid, and the amides of said acids;

and b) transesterifying or esterifying the poly(meth)acrylate containing hydroxy-functional side chains with a (meth)acrylate or (meth)acrylic acid, preferably with methyl, ethyl, 2-ethylhexyl or butyl(meth)acrylate, in the presence if desired of stabilizers selected from the group consisting of 2,6-dibutylphenols such as di-tert-butylphenol, p-cresol, hydroquinone, dimethylhydroquinone, phenothiazines and phosphorous esters, in the presence of an enzyme which catalyzes the transesterification or esterification.

"(Meth)acrylic acid" is used as an abbreviation for "methacrylic acid or acrylic acid"; correspondingly, "(meth)acrylate" is used as an abbreviation for "methacylate or acrylate".

The process of the invention enables functional groups, especially (meth)acrylic groups, to be introduced gently into poly(meth)acrylates without the likelihood of cleavage of the ester groups of the poly(meth)acrylate. Moreover, it is possible to prepare the functionalized polymers starting from poly(meth)acrylates containing hydroxy-functional side chains, which are substantially less expensive than glycidyl-functionalized poly(meth)acrylates used hitherto in the prior art.

Step a)

In a preferred embodiment of the process of the invention step a) is carried out using 10 to 80% by weight, preferably 20 to 80% by weight, more preferably 30 to 70% by weight of component A, and 10 to 80% by weight, preferably 20 to 70% by weight, more preferably 20 to 60% by weight of component B, and 0 to 50% by weight, preferably 0 to 40% by weight, more preferably 5 to 25% by weight of component C, and 0 to 15% by weight, preferably 0 to 10% by weight, more preferably 0.5 to 5% by weight of component D.

The poly(meth)acrylates used in accordance with the invention, containing hydroxy-functional side chains, can be prepared by various methods known to the skilled worker. Preference is given to their preparation by free-radical polymerization.

The polymerization takes place in general by emulsion, solution or bulk polymerization, preference being given to emulsion polymerization or solution polymerization.

In one embodiment the poly(meth)acrylates containing hydroxy-functional side chains are prepared by emulsion polymerization. In the case of emulsion polymerization components A, B, and, where appropriate, C and, where appropriate, D are reacted with one another in the presence of water, emulsifiers, initiators, and, where appropriate, regulators.

Emulsifiers used are generally anionic, nonionic, cationic or amphoteric emulsifiers, with anionic or nonionic emulsifiers being preferred. Suitable anionic emulsifiers are sodium, potassium or ammonium salts of long-chain aliphatic carboxylic acids and sulfonic acids, alkali metal $C_{12-16}$ alkyl sulfates, oxethylated and sulfated or sulfonated long-chain aliphatic alcohols or alkylphenols, and sulfodicarboxylic esters. Suitable noninic emulsifiers are oxethylated fatty alcohols and alkylphenols, the ethylene oxide units possibly amounting to between 2 and 50 mol/mol. Suitable cationic emulsifiers are ammonium, phosphonium, and sulfonium compounds including at least one long aliphatic hydrocarbon chain as a hydrophobic moiety. It is also possible to use a combination of different emulsifiers: for example, ionic and nonionic emulsifiers.

The water used is preferably distilled or deionized, since salts may affect the stability of the emulsion. Generally speaking, the polymerization process is carried out under nitrogen, since oxygen inhibits the polymerization.

The molecular weight of the poly(meth)acrylates containing hydroxy-functional side chains can be lowered by adding regulators. Suitable regulators are, for example, halogenated compounds such as carbon tetrachloride, carbon tetrabromide, bromal, benzyl bromide, and trichlorobromomethane, or mercaptans such as butyl mercaptan or dodecyl mercaptan or Rongalit® C.

Suitable initiators are in general all initiators known to the skilled worker for polymerizing (meth)acrylates. Use is made in general of water-soluble peroxo compounds such as alkali metal or ammonium persulfate, hydrogen peroxide or tert-butyl peroxyethylhexanoate. Also suitable are redox systems such as $H_2O_2$-ascorbic acid, $H_2O_2$-Fe(II)/Fe(III), $H_2O_2$-Ce (IV), persulfites-Fe, metabisulfites-Fe or hydroperoxides-metal salts. The initiators are used generally in an amount of 0.05 to 8% by weight, preferably 0.2 to 2% by weight, based on amount of monomers used.

Any initiators still present after the polymerization can be deactivated after the polymerization in order to prevent possible polymerization of the poly-(meth)acrylates prepared in accordance with the invention in step b). The deactivation is generally accomplished by adding a reducing agent, e.g., ascorbic acid.

The polymerization is generally conducted within a temperature range from 30 to 120° C., preferably 40 to 110° C., more preferably 50 to 90° C. The polymerization is generally conducted under a pressure of 1 to 20, preferably 1 to 15 bar, more preferably 1 to 5 bar.

The emulsifiers are generally used in an amount of 0.5 to 15% by weight, preferably of 0.5 to 10% by weight, more preferably 0.5 to 5% by weight, based on the amount of components A, B, if desired, C, and, if desired, D that are used.

The particle diameter of the poly(meth)acrylates containing hydroxy-functional side chains that are obtained after polymerization is generally 20 to 1000 nm, preferably 20 to 500 nm, more preferably 50 to 400 nm, determined by means of light scattering.

The pH during the emulsion polymerization is generally between 1 and 6, preferably between 2 and 6. The hydroxyl numbers are generally at least 20 to 180, preferably at least 40 to 120. The solids content of the dispersions is generally 10 to 50, preferably 20 to 40, and the glass transition temperature of the polymers obtained is generally between −40 and +80° C.

The resultant poly(meth)acrylates containing hydroxy-functional side chains generally have an average molecular weight of 1000 to 2 000 000, preferably 1000 to 1 000 000, more preferably 50 000 to 500 000. The average molecular weight was determined by means of gel permeation chromatography (GPC). The molecular weight in question is the number-average molecular weight.

The poly(meth)acrylates containing hydroxy-functional side chains can be prepared by means of a one-pot or batch procedure, feed techniques, and continuous procedures. The conduct of said procedures is known to the skilled worker.

The poly(meth)acrylate containing hydroxy-functional side chains that is obtained in step a) can be isolated by methods known to the skilled worker. One embodiment is described, for example, in EP-A 0 029 637, but in the process according to the present specification hydroxyl-free solvents are used, or in a second step a hydroxyl-containing solvent is replaced by a hydroxyl-free solvent. For use in step b) of the process of the invention the poly(meth)acrylate containing hydroxy-functional side chains, following its isolation, is used in water-free form.

In another preferred embodiment the poly(meth)acrylates containing hydroxy-functional side chains are prepared by solution polymerization. In the solution polymerization the components A, B, and, where appropriate, C and, where appropriate, D are reacted with one another in the presence of a solvent, initiator and, where appropriate, regulators.

Initiators suitable for the solution polymerization are peroxides such as dialkyl peroxides, e.g., di-tert-butyl peroxide and di-tert-amyl peroxide, peroxy esters such as tert-butyl peroxy-2-ethylhexanoate and tert-amyl peroxy-2-ethylhexanoate, diacyl peroxides such as benzoyl peroxide, lauroyl peroxide, and decanoyl peroxide, percarbonates such as tert-butyl peroxyisopropyl carbonate, di-2-ethylhexyl peroxydicarbonate, perketals and ketone peroxides, and also azo initiators such as 2,2'-azobis(2,4-dimethylpentanenitrile), 2,2'-azobis(2-methylpropanonitrile), 2,2'-azobis(2-methylbutanonitrile), 1,1'-azobis(cyclohexanecarbonitrile), 2,2'-azobis(2,4,4-trimethylpentane), and 2-phenylazo-2,4-dimethyl4-methoxyvaleronitrile.

Preferred solvents are those not disruptive to an enzymatic reaction in accordance with step b), so that removal of the solvent prior to execution of step b) is unnecessary. Particular preference is given to solvents selected from methyl isobutyl ketone, acetone, xylene, N-methylpyrrolidone, methyl ethyl ketone, methyl propyl ketone, methyl amyl ketone, and solvent naphtha.

Step b)

In step b) the poly(meth)acrylate containing hydroxy-functional side chains is transesterified or esterified with at least one (meth)acrylate or (meth)acrylic acid or a stabilizer in the presence of an enzyme which catalyzes the transesterification or esterification. Preference is given to carrying out a transesterification with methyl, ethyl, 2-ethylhexyl or butyl (meth) acrylate.

The enzymatic transesterification or esterification with a (meth)acrylate or (meth)acrylic acid takes place in general at low temperatures, preferably 10 to 100° C., more preferably 20 to 80° C. The reaction conditions during the enzymatic transesterification or esterification are mild. The low temperatures and other mild conditions prevent the formation of-by-products-in step b), which may otherwise originate, for example, from chemical catalysts or as a result of unwanted free-radical polymerization of the (meth)acrylate used or of the (meth)acrylic acid used, which can otherwise be prevented only by adding stabilizers.

For the enzymatic reaction (step b)) the product from step a) can be used in general without further pretreatment. If required, the product may be freed from volatiles (e.g., solvents) or additional substances (e.g., solvents) may be added. Specifically, it should as far as possible be free from free-radical initiators or have a low free-radical initiator content.

Preferred enzymes used are hydrolases, especially hydrolases selected from the group consisting of lipases, esterases, and proteases. The enzymes can be used in free form or in immobilized form on a support to which they have been chemically or physically bound. The amount of the enzyme catalyst is preferably 0.1 to 20% by weight, more preferably 1 to 10% by weight, based on the poly(meth)acrylate containing hydroxy-functional side chains that is used.

The reaction time depends among other things on the amount used and on the activity of the enzyme catalyst and the desired degree of conversion, and also on the hydroxy-functional side chain of the poly(meth)acrylate.

The (meth)acrylate used for the transesterification or the (meth)acrylic acid used for the esterification is generally employed in equimolar amounts or in excess in relation to the number of hydroxy-functional side chains in the poly(meth) acrylate. Preference is given to using a molar ratio of (meth) acrylate or (meth)acrylic acid to hydroxy groups in the side chains of the poly(meth)acrylate of 1:1 to 10:2. Higher excesses are not disruptive.

Generally speaking, in step b), 20-100%, preferably 40 to 100%, more preferably 60 to 100% of all hydroxy-functional side chains originally present in the poly(meth)acrylate are reacted with a (meth)acrylate or (meth)acrylic acid.

Suitable stabilizers, used where appropriate, are selected from the group consisting of 2,6-dibutylphenols such as di-tert-butylphenol, p-cresol, hydroquinone, dimethylhydroquinone, phenothiazines, and phosphorous esters. It is, however, also possible to carry out step b) without using stabilizers.

The reaction can be carried-in all reactors suitable for such a reaction. Reactors of this kind are known to the skilled worker. The reaction takes place with preference in a stirred tank reactor, a fixed bed reactor or a Taylor reactor.

The alcohol formed or the water of reaction formed during the transesterification or esterification can be removed by methods known to the skilled worker: for example, by absorption (with molecular sieve, for example), distillation or pervaporation.

The reaction is continued until the desired conversion, generally 5 to 100%, has been reached. In the case of a reaction regime with simultaneous removal of the water or alcohol formed during the reaction it is possible to achieve higher conversions in shorter reaction times owing to the shifting of the reaction equilibrium.

Following the reaction the enzyme catalyst can be separated off by appropriate measures, filtration or decanting for example, and can if desired be used a number of times.

A further subject of the present specification are UV-curable and/or dual-cure poly(meth)acrylates preparable by the process of the invention. Owing to the mild reaction conditions in the process of the invention it is possible to obtain new kinds of (meth)acryloyl-functional poly(meth)acrylates without the risk of cleavage of the ester bonds in the poly (meth)acrylates by acid catalysis or high temperatures.

These (meth)acryloyl-functional poly(meth)acrylates of the invention are suitable as binders in radiation-curable or dual-cure coating materials: for example, in topcoats such as transparent clearcoat materials, but also in undercoat materials, primers, and surfacers. The (meth)acryloyl-functional poly(meth)acrylates have excellent weather stability. In conjunction with a curing technology (radiation cure or dual cure) it is possible to obtain further advantages: for example, an increase in the scratch resistance of a coating. Particularly decisive, however, is the improvement in application through use of the (meth)acryloyl-functional poly(meth)acrylates of the invention, since they allow rapid drying.

A further subject of the present specification is therefore the use of the (meth)acryloyl-functional poly(meth)acrylates of the invention or of those prepared by the process of the invention as binders in radiation-curable or dual-cure coating materials, preferably in topcoats, more preferably in transparent clearcoat materials.

By "dual-cure" is meant that the materials are curable thermally and with actinic radiation. In the context of the present invention actinic radiation means electromagnetic radiation such as visible light, UV radiation or X-rays, especially UV radiation, and corpuscular radiation such as electron beams.

Radiation-curable binders are those curable by means of actinic radiation as defined above, in particular by means of UV radiation.

A further subject of the present specification are coating formulations comprising the (meth)acryloyl-functional poly (meth)acrylates of the invention or those preparable by the process of the invention. The (meth)acryloyl-functional poly (meth)acrylates or the stabilizer-functionalized poly(meth) acrylates can be used both in basecoat materials and in topcoat materials. In view of their particular properties such as the enhancement of scratch resistance in conjunction with high UV stability of a coating their use in topcoats is preferred.

Generally speaking, the composition of the topcoat is selected such that the cured topcoat material has a storage modulus E' in the rubber-elastic range of at least $10^{7.6}$ Pa, preferably of at least $10^{8.0}$ Pa, more preferably of at least $10^{8.3}$ Pa, and a loss factor at 20° C. of not more than 1.10, preferably not more than 0.06, the storage modulus E' and the loss factor tanδ having been measured by dynamic-mechanical thermoanalysis on homogeneous free films with a thickness of 40±10 μm. The loss factor tanδ is defined as the quotient of the loss modulus E" and the storage modulus E'.

Dynamic-mechanical thermoanalysis is a general measurement method for determining the viscoelastic properties of coatings and is described, for example, in Murayama T., Dynamic Mechanical Analysis of Polymeric Material, Elsevier, New York, 1978 and Loren W. Hill, Journal of Coatings Technology, Vol. 64, No. 808, May 1992, pp. 31 to 33. The measurements can be carried out, for example, using the instruments II, MKIII, or MKIV from the company Rheometrics Scientific.

The radiation-curable or dual-cure topcoats preferably have a viscosity at 23° C. of < than 100 s efflux time in the DIN4 cup, more preferably <80 s efflux time in the DIN4 cup. For casting application and roller application the viscosity may also be above this.

The topcoats of the invention comprise in addition to the (meth)acryloyl-functional poly(meth)acrylates of the invention, if desired, one or more photoinitiators and, if desired, customary auxiliaries and additives. Suitable photoinitiators are customary photoinitiators used in radiation-curable or dual-cure coating materials, examples being benzophenones, benzoins or benzoin ethers, preferably hydroxyacrylic ketones and bis(acyl)phosphine oxides. It is also possible, for example, to use those in commerce under the name Irgacure® 184, Irgacure® 1800, and Irgacure® 500 from Ciba Geigy, Genocure® MBF from Rahn, and Lucirin® TPO from BASF AG.

Suitable further auxiliaries and additives are, for example, light stabilizers (for example HALS compounds, benzotriazoles, oxalanilid, et cetera), slip additives, polymerization inhibitors, flatting agents, defoamers, leveling agents, and film-forming auxiliaries, cellulose derivatives for example, et cetera. Additionally it is possible to use rheology control components, such as organic urea compounds, urethane urea compounds and/or $SiO_2$.

The topcoats of the invention are employed in particular as clearcoat materials, so that they normally contain no hiding pigments and no fillers, or only transparent fillers. Also possible, however, is their use in the form of pigmented topcoats. In that case the topcoats additionally comprise pigments. Furthermore, in this case the topcoats may comprise one or more fillers.

A further subject of the present application are therefore topcoats comprising 5 to 80% by weight, preferably 10 to 60% by weight, more preferably 20 to 50% by weight of at least one (meth)acryoyl-functional poly(meth)acrylate of the invention or one prepared by the process of the invention, 0.5 to 15% by weight, preferably 1 to 10% by weight, more preferably 1 to 5% by weight of at least one photoinitiator, 0.5 to 8% by weight, preferably 1 to 6% by weight, more preferably 1 to 4% by weight of further auxiliaries and additives, 0 to 40% by weight, preferably 0 to 30% by weight, more preferably 0 to 25% by weight of pigments, and 0 to 40% by weight, preferably 0 to 30% by weight, more preferably 0 to 25% by weight of at least one filler, such as transparent metal oxides, $BaSO_4$, and waxes.

Preferred (meth)acryloyl-functional poly(meth)acrylates, photoinitiators, auxiliaries and additives, and fillers and pigments have already been specified above. the topcoat of the invention, in which the (meth)acryloyl-functional poly(meth) acrylate, the photoinitiator, if desired further auxiliaries and additives, The topcoats of the invention are prepared by mixing the individual components in accordance with methods known to the skilled worker in apparatus known according to the skilled worker.

A further subject of the present specification is therefore a process for preparing and, if desired, fillers and pigments are mixed with one another.

The topcoats of the invention are generally applied to substrates coated with a basecoat material. They may be applied by what is known as coil coating or by injection molding to the substrates. Such substrates are, for example, metal sheets, or metal strips and plastics of any kind, e.g., automobile bodies and motorcycle parts.

After the topcoat has been applied it is subjected to a radiation cure or dual cure. The equipment and conditions for these curing methods are known from the literature and require no further description (for radiation curing see, for example, R. Holmers, UV and E. B. Curing Formulations for Printing Inks, Coatings and Paints, SITA Technology, Academic Press, London, United Kingdom 1984).

The examples which follow provide further illustration of the invention.

EXAMPLES

1 Preparation of a hydroxy-functional binder

| | Formula: | | |
|---|---|---|---|
| Initial charge | Methyl isobutyl ketone | | 540.0 g |
| Monomers | Styrene | 10.00% by wt.[1] | 123.6 g |
| | EHA (2-ethylhexyl acrylate) | | |
| | HEMA (hexylethyl methacrylate) | 46.50% by wt.[1] | 574.4 g |
| | HBA (hydroxybutyl acrylate) | | |
| | AA (acrylic acid) | 27.00% by wt.[1] | 336.6 g |
| | | 15.00% by wt.[1] | 185.2 g |
| | | 1.50% by wt.[1] | 18.6 g |
| rinse | Methyl isobutyl ketone | | 5.0 g |
| Initiator | tert-Butyl peroxy-2-ethylhexanoate | 8% by wt.[2] | 98.8 g |
| | Methyl isobutyl ketone | | 74.2 g |
| rinse | Methyl isobutyl ketone | | 46.6 g |
| End | | | 2000.0 g |

[1] based on the sum of the components styrene, EHA, HEMA, HBA, AA
[2] based on the sum of the components styrene, EHA, HEMA, HBA, AA Procedure:

Weigh out initial charge and heat to 110° C. At constant temperature, meter monomers and initiator into the reactor at a uniform rate. After 4 hours the monomer feed is at an end. After 4.5 hours the initiator feed is at an end. After the end of the metering of initiator polymerization is continued for 1 hour, followed by cooling and discharge of the reaction mixture obtained.

| *end values: | |
|---|---|
| Solids (1 h, 130° C.): | 66.3% |
| OH number (theoretical) total: | 174.8 mg/g (determined to DIN 43402) |
| OH number (practical): | 165 mg/g (determined to DIN 53246) |
| GC (residual monomer content)[3)]: | EHA 0.3%; AA < 0.3% all others < 0.1% |
| GPC[4)]  $M_n$[5)] | 5829 |
| $M_w$[6)] | 20 722 |
| $M_w/M_n$[7)] | 3.55 |

[3)]GC = gas chromatography
[4)]GPC = gel permeation chromatography (with polystyrene standard)
[5)]Mn = number-average molecular weight
[6)]$M_w$ = weight-average molecular weight
[7)]$M_w/M_n$ = polydispersity 2. Preparation of a UV-Active Polyacrylate Batch: 300 ml of polymer solution in methyl isobutyl ketone from Example 1
    300 g of methyl acrylate (MA)
    150 mg of methoxyphenol
    150 g of 5 Å mole sieve
    30 g of Novozym® 435 (immobilized lipase from Candida antarctica from the company Novozymes)

The components stated are stirred at 40° C. for 72 hours. The reaction mixture is subsequently filtered and the polyacrylate obtained is washed with methyl isobutyl ketone (MIK). The excess MA and MIK is removed in vacuo on a rotary evaporator at 60° C. to 70° C. This gave 227 g of target product. The fraction of the acrylated hydroxy groups was determined as being about 34% by means of the OH number.

The OH number was determined in accordance with a method which is known in the prior art (DIN 53240, Part 2).

3. Preparation of a UV Coating Formulation

| a) Stock varnish | |
|---|---|
| inventive UV polyacrylate | 32.5 |
| Sartomer ® 399 | 30.6 |
| Thixharz ® SCA | 11.5 |
| (basis: benzylamine/hexamethylene diisocyanate) | |
| Irgacure ® 184 (photoinitiator) | 0.8 |
| Lucirin ® TPO (photoinitiator) | 0.4 |
| Byk ® 358 (leveling assistant) | 0.2 |
| Tinuvin ® 292 (free-radical scavenger) | 1.0 |
| Tinuvin ® 400 (UV absorber) | 1.0 |
| Butyl acetate | 22.0 | b) Curing agent mixture

A curing agent mixture composed of 72.7 parts of Roskydal® UA VP LS 2337 (unsaturated isophorone diisocyanate), 18.2 parts of Roskydal® UA VP FWO 3003 77 and 9.1 parts of butyl acetate is added (the parts are parts by weight).

The components were mixed with a dissolver.

4. The Coating Formulation was Applied by Spray Application.

5. Variation of the hydroxy-Functional Units

As the following examples show, different hydroxy-functional units can be used. The examples mentioned are not, however, intended to be any restriction. The polymer solutions were prepared by methods corresponding to Example 1.

10 g of polymer solution, 10 g of methyl acrylate, 5 g of mole sieve (5 Å) and 1 g of immobilized lipase (Novozym® 435) were shaken at 40° C. for 72 hours. After filtration and concentration, the conversion was determined by way of the OH number.

| Polymer solution | Esterified unit | Conversion [%] |
|---|---|---|
| 2 | Hydroxyethyl acrylate | 34 |
| 3 | Hydroxyethyl acrylate | 41 |
| 4 | Hydroxyethyl methacrylate | 12 |
| 5 | Hydroxyethyl methacrylate | 22 |
| 6 | Hydroxyethyl methacrylate | 47 |
| 7 | Hydroxybutyl acrylate | 67 |
| 8 | Hydroxybutyl acrylate | 80 |

6. Reaction Optimization

It was possible to optimize the reaction conditions by varying the reaction time, the added amount of methyl acrylate, and mole sieve. The polymer solutions shown in the table under Example 5 were reacted under the following optimized reaction conditions.

10 g of polymer solution, 2 g of methacrylate, 2 g of mole sieve and 1 g of Novozym® 435 were shaken at 40° C. for 24 hours. After filtration and concentration, the conversion was determined by way of the OH number.

| Polymer solution | Conversion [%] |
|---|---|
| 2 | 23 |
| 3 | 39 |
| 5 | 6 |
| 6 | 17 |
| 7 | 40 |
| 8 | 46 |

The invention claimed is:

1. A process for preparing poly(meth)acrylates curable with at least one of actinic radiation or dual-cure utilizing actinic radiation and thermal cure, comprising the following steps:
  a) preparing a poly(meth)acrylate containing hydroxy-functional side chains by polymerizing
    aa) at least one (meth)acrylate of the general formula (I) as component A

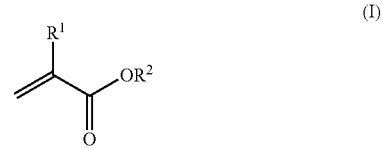

(I)

in which
  $R^1$ is H, $CH_3$ or $CH_2OH$ and
  $R^2$ is an alkyl radical which is unsubstituted or substituted by functional groups chosen from the group consisting of acrylic, ether, amino, epoxy, halogen and sulfonic acid groups, and
  ab) at least one hydroxyalkyl (meth)acrylate of the general formula (II) as component B

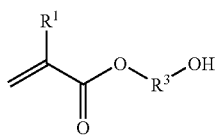

in which
R¹ is H, CH₃ or CH₂OH and
R³ is —(CH₂)$_n$—, —CH₂—CH(CH₃)—CH₂— or —CH₂CH(CH₃)— or —CH(CH₃)CH₂— or

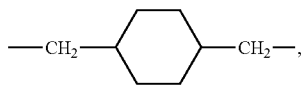

n is at least 2, and
ac) if desired, further comonomers, copolymerizable with the (meth)acrylates of the general formula (I) and (II), as component C, and
ad) if desired, auxiliary monomers as component D; and
b) transesterifying or esterifying the poly(meth)acrylate containing hydroxy-functional side chains with a (meth)acrylate or (meth)acrylic acid in the presence of an enzyme which catalyzes the transesterification or esterification.

2. A process as claimed in claim 1, wherein step a) is carried out using
10 to 80% by weight of component A,
10 to 80% by weight of component B,
0 to 50% by weight of component C, and
0 to 15% by weight of component D.

3. A process as claimed in claim 1, wherein enzymes used in step b) are hydrolases selected from the group consisting of lipases, esterases, and proteases.

4. A process as claimed in claim 1, wherein step b) is carried out using methyl, ethyl, 2-ethyihexyl or butyl (meth)acrylate.

5. A process as claimed in claim 1, wherein the temperature at which step b) is conducted is 20 to 100° C.

6. A process as claimed in claim 1, wherein component B is selected from the group consisting of 2-hydroxyethyl (meth)acrylate, 2-hydroxypropyl (meth)acrylate, and hydroxybutyl (meth)acrylate.

7. A process as claimed in claim 1, wherein 5 to 100% of the side chains of the poly(meth)acrylate prepared in accordance with step a) have been (meth)acrylated.

8. Poly(meth)acrylates prepared by a process as claimed in claim 1.

9. A topcoat containing
5 to 80% by weight of at least one poly(meth)acrylate prepared according to claim 1 comprising
0.5 to 15% by weight of at least one photoinitiator,
0.5 to 8% by weight of further auxiliaries and additives,
0 to 40% by weight of pigments, and
0 to 40% by weight of at least one filler.

10. A process for preparing a coating formulation as claimed in claim 9, in which the individual components are mixed with one another.

11. A dispersion comprising the poly(meth) acrylate of claim 8.

12. A coating composition comprising the poly(meth)acrylate of claim 8.

13. A coating composition comprising the poly(meth)acrylate of claim 8 selected from primers, surfacers and topcoats.

14. A topcoating composition comprising the poly(meth)acrylate of claim 8.

15. A transparent clearcoat composition comprising the poly(meth)acrylate of claim 8.

16. A process for preparing dispersions or coating formulations comprising the step of adding poly(meth)acrylates curable with actinic radiation or both actinic radiation and thermal cure as claimed in claim 8 as binders to dispersions or coating formulations.

* * * * *